(12) United States Patent
Smeets et al.

(10) Patent No.: US 8,758,698 B2
(45) Date of Patent: Jun. 24, 2014

(54) COMBUSTION TUBE AND METHOD FOR COMBUSTING A SAMPLE FOR COMBUSTION ANALYSIS

(75) Inventors: Louis Marie Smeets, Amsterdam (NL); Fransiscus Maria Folst, Capelle aan Den IJssel (NL); Peter Joannes Coenders, Woerden (NL)

(73) Assignee: Thermo Fisher Scientific Inc., Waltham, MA (US)

( * ) Notice: Subject to any disclaimer, the term of this patent is extended or adjusted under 35 U.S.C. 154(b) by 286 days.

(21) Appl. No.: 12/054,006

(22) Filed: Mar. 24, 2008

(65) Prior Publication Data

US 2008/0299670 A1    Dec. 4, 2008

(30) Foreign Application Priority Data

Mar. 23, 2007    (GB) .................................. 0705650.0

(51) Int. Cl.
*G01N 25/24*    (2006.01)
*G01N 31/12*    (2006.01)
(52) U.S. Cl.
USPC .......................................... 422/224; 422/170
(58) Field of Classification Search
USPC ............ 422/78, 93; 73/863.41; 436/155, 158, 436/160
See application file for complete search history.

(56) References Cited

U.S. PATENT DOCUMENTS

| | | | |
|---|---|---|---|
| 2,992,676 A * | 7/1961 | Henwood | ...................... 431/215 |
| 3,909,202 A | 9/1975 | Becker et al. | |
| 5,236,353 A | 8/1993 | Adani et al. | |
| 5,259,755 A * | 11/1993 | Irwin et al. | ......................... 431/9 |
| 5,879,148 A | 3/1999 | Cheng et al. | |
| 6,458,328 B1 | 10/2002 | Wreyford | |
| 7,182,920 B2 * | 2/2007 | Carroni et al. | ................. 422/180 |

FOREIGN PATENT DOCUMENTS

| | | |
|---|---|---|
| DE | 31 49 550 A1 | 6/1983 |
| EP | 1 621 815 A1 | 2/2006 |
| GB | 114969 | 4/1918 |
| GB | 774005 | 5/1957 |
| SU | 756132 | 8/1980 |
| WO | WO 2005/043037 A1 | 5/2005 |

OTHER PUBLICATIONS

Search Report issued Mar. 23, 2007 by the European Patent Office for British Patent Application No. 0705650.0 (5 pages).
Combined Search and Examination Report issued Jul. 12, 2007 by the UK Intellectual Property Office for British Patent Application No. 0705650.0 (4 pages).
Search Report issued Nov. 6, 2007 by the UK Intellectual Property Office for British Patent Application No. 0705650.0 (2 pages).

* cited by examiner

*Primary Examiner* — Christopher A Hixson
(74) *Attorney, Agent, or Firm* — Thomas F. Cooney; Charles B. Katz; Haynes and Boone, LLP

(57) ABSTRACT

Combustion tube (100,130,150) and method for combusting a sample to form combustion products for analysis. A primary combustion chamber (102) receives and combusts a sample to form first combustion products. A secondary combustion chamber (110) receives and combusts the first combustion products to form second combustion products. The secondary chamber is disposed around the primary chamber and comprises a plurality of—preferably, three—combustion compartments (112-116). Each successive compartment is disposed around the preceding compartment and defines a respective gas flow channel having an inlet opening (108,118, 120) and an outlet opening (118,120,122) at opposite ends. Each successive gas flow channel shares its inlet opening with the outlet opening of the preceding channel. The plurality of combustion compartments define a substantially continuous gas flow conduit from the inlet opening of the innermost compartment to the outlet opening of the outermost compartment. Static gas mixers (132,134) may be employed to enhance mixing of the combustion products.

17 Claims, 6 Drawing Sheets

COMBUSTION TUBE AND METHOD FOR COMBUSTING A SAMPLE FOR COMBUSTION ANALYSIS

FIELD OF THE INVENTION

The invention relates to a combustion tube and method for combusting a sample for combustion analysis of the sample.

BACKGROUND

Combustion analyzers are used to determine the concentration of one or more components of a sample, by combusting the sample and analysing the gaseous products for specific oxides. Typically, the carbon, sulphur and/or nitrogen content of the sample is measured by detecting $CO_2$, $SO_2$ and NO, respectively.

A schematic illustration of a typical combustion analyzer is shown in FIG. 1. The combustion analyzer 10 comprises a sample introduction stage 20, a combustion stage 30, a conditioning stage 40, and a detection stage 50. The sample introduction stage 20 comprises a sample introduction apparatus 22, to which are connected a supply of a sample 24, a supply of oxygen 26 and a supply of argon 27. The sample introduction apparatus 22 introduces these fluids into a combustion tube 32 in a suitable form for combustion to take place. A further supply of oxygen 25 may be provided, directly into the combustion tube 32. The combustion tube 32 is heated by an electric heater 34, so that the sample is delivered into an oxygen-rich atmosphere at high temperature, typically around 1000° C. The sample is thereby converted into various combustion products, such as $CO_2$, $H_2O$, $SO_2$, $NO_x$, etc. The combustion products leave the combustion tube 32 and pass through the conditioning stage 40, where processes such as cooling, filtering, drying, etc. take place. The conditioned products then pass through one or more dedicated detectors 52, 54, in which properties of the components of the combustion products may be detected. For example, $CO_2$ may be detected by absorption of infrared radiation, using a non-dispersive infrared (NDIR) detector; $SO_2$ may be detected by fluorescence with ultraviolet light, using a light sensor; and NO can be detected from de-excitation processes following its reaction with ozone ($O_3$) to form excited $NO_2$, using a chemiluminescence light sensor. The detected signals are indicative of the respective amount of each component of the combustion products and can therefore be related to the composition of the original sample. Finally, the detected combustion products are passed out of the detection stage 50, as waste products 56.

The performance of such a combustion analyzer 10—in terms of its suitability, reliability, accuracy and robustness—depends strongly on the performance of the combustion tube, in particular its ability to convert the element(s) of interest in a sample into its/their respective oxide(s).

Various combustion tube forms are known. One type of prior art combustion tube is simply a single, straight tube, such as the combustion tube 60 of the hydrogen sulphide analyzer 58, shown in FIG. 2. A supply of a sulphur-containing sample 62 and a supply of air 64 are provided to the combustion tube 60 at one end. The sample and air pass down the combustion tube 60, which extends within a heater 66, and the sample is combusted in the combustion tube 60 to produce sulphur dioxide. The downstream end of the combustion tube 60 opens into a hydrogenation chamber 68, which also extends within the heater 66. The sulphur dioxide passes into the hydrogenation chamber 68, along with a supply of hydrogen 70, and the sulphur dioxide is reduced to hydrogen sulphide ($H_2S$). The hydrogen sulphide leaves the hydrogenation chamber 68 at a downstream end and passes out of an outlet pipe 72 to a lead acetate tape detector (not shown).

The combustion tube 60, while very simple, does not have good gas-mixing properties; that is, the sample and air flowing through the combustion tube 60 are not encouraged to mix, so localised regions of incomplete combustion may result. Given the limited opportunity for a sample to be combusted in the combustion tube 60 before entering the hydrogenation chamber 68 (or any other downstream processing device, if the combustion tube 60 is used with a different analyzer) and the poor mixing performance of the tube, a single, straight-sided tube has a number of disadvantages.

To mitigate the disadvantages of such a combustion tube, it is known to provide a catalyst inside the combustion tube, to promote sample combustion. It is also known to place a number of quartz beads inside the combustion tube, to promote mixing of the sample and oxygen. However, catalysts degrade over time and tend to promote oxidation of some components better than others, so catalysts need to be replaced regularly and analyzers need to be re-calibrated often. Also, while the beads work to some extent, any movement of them, resulting from movement of the combustion tube, will change the characteristics of the tube and therefore its combustion efficiency, again requiring re-calibration of the analyzer.

One alternative approach is proposed in U.S. Pat. No. 3,909,202. Here, a combustion tube comprises two tubes arranged one inside the other and surrounded by an outer shell. A sample for combustion is injected into the inner tube and passes through the diverting tube and into the outer shell. The gaseous combustion products are then delivered to an analyzer through an outlet opening in the outer shell.

Another approach, which is currently in use, is shown in FIG. 3. This combustion tube 74 is known as a "turbo tube" and is used in nitrogen, sulphur and halogens (NSX) combustion analyzers. The turbo tube 74, which is made of quartz, has an inlet port 76 for receiving supplies of a sample and oxygen 78,79. The inlet port leads into a primary chamber 80, which itself leads into a so-called turbo chamber 82. The two chambers are separated by a partition 84, which comprises an opening 86. The opening leads into a helical tube 88, which extends from the partition on its downstream side, i.e. into the turbo chamber 82. At the downstream end of the turbo chamber 82, there is an inlet tube 90 through which a further supply of oxygen 92 is provided, into the turbo chamber. There is also an outlet tube 93, which extends from outside the turbo chamber 82, into the chamber and through the space defined within the helical tube 88, towards the partition 84.

In use, a sample 78 is introduced into the primary chamber 80 along with a flow of oxygen 79. The turbo tube 74 is heated to a high temperature, which effects thermal cracking and combustion of the sample in the primary chamber 80. The combustion products pass into the turbo chamber 82 through the helical tube 88, which opens into the chamber towards its downstream end. The further supply of oxygen 92 is added to the combustion products with the aim of achieving complete combustion of the as-yet-uncombusted sample components. The final combustion products 94 flow out of the turbo tube 74 along the outlet tube 93, to gas conditioning and detection stages (not shown).

Although the above two combustion tubes may perform satisfactorily in practice, a number of disadvantages can nevertheless be identified. Firstly, both combustion tubes have a relatively high space demand; for example, to accommodate the various inlet and outlets ports and tubes at each end of the combustion tubes. The turbo tube, in particular, is relatively long, at around 40 cm, and needs a relatively bulky heater to surround it. These factors lead to a relatively large footprint for a combustion analyzer using one of these combustion tubes.

Secondly, the gas mixing capabilities and flow characteristics of the combustion tubes are not especially favourable. The helical tube 88 of the turbo tube 74 does effect some gas mixing, due to the difference in the speed of gas flowing on the inside and on the outside of the helix. However, at the gas flow rates used in combustion analysis, the fluid flow in the combustion tubes tends to be generally laminar and little mixing occurs. Poor sample and oxygen mixing can result in local oxygen deficiencies, leading in some circumstances to the production of soot. If combustion products including soot are allowed to leave the combustion tube and pass downstream to the gas conditioner(s) and/or detector(s), these devices will become contaminated and in need of manual cleaning.

Thirdly, it takes a relatively long time to purge, or flush out, the combustion products from the combustion tubes, following combustion of a sample, before another sample may be combustion analyzed. For both combustion tubes, the time required to flush them out may be as much as around 2 minutes. With the turbo tube 74, this disadvantage is exacerbated by the differences in density between the combustion products and the oxygen carrier gas. The more dense combustion gases—mainly $CO_2$ and $H_2O$—tend to flow along the bottom of the combustion tube, while the less dense oxygen flows along the top. This phenomenon can result in erratic gas flow behaviour in the combustion tube 74, especially at the beginning or end of a combustion procedure. This problem also applies to the U.S. Pat. No. 3,909,202 combustion tube, in particular as a result of the provision of an additional combustion chamber 8 at the bottom of the outer shell, for pre-combustion of the air carrier gas.

Accordingly, it would be desirable to provide an improved or alternative—in particular, a more combustion efficient—combustion tube and method for combustion analysing a sample. This invention aims to provide a combustion tube and method for combustion analysing a sample which address some or all of the above problems.

SUMMARY

According to one aspect of the invention, there is provided a combustion tube for receiving a sample for combustion thereof to form combustion products, the combustion tube comprising: a primary combustion chamber for receiving a sample for combustion thereof to form first combustion products; and a secondary combustion chamber for receiving the first combustion products for further combustion thereof to form second combustion products, the secondary chamber being disposed around the primary chamber and comprising a plurality of combustion compartments, each successive compartment being disposed around the preceding compartment and each compartment defining a respective gas flow channel having an inlet opening at one end and an outlet opening at the opposite end, wherein each successive gas flow channel shares its inlet opening with the outlet opening of the preceding channel.

The inlet and outlet openings are provided at opposite ends of each respective compartment; that is, at or very close to each extremity of the compartment. This means that gas flowing into a compartment is immediately guided towards that compartment's outlet opening, which itself leads directly into the next compartment. As a result, the gas is generally urged onwards through each compartment in turn and does not stagnate or languish in 'dead' spaces outside the gas flow channel. This means that gas flowing into the secondary chamber is urged through the compartments and out of the secondary chamber by gas flowing in behind it. Consequently, sample throughput times may be reduced, because it does not take so long for the combustion products from that sample to pass through the combustion tube. Also, the time taken to flush out the tube between samples may be reduced, because a flushing gas can pass through the tube relatively quickly and because smaller quantities of the sample and/or its combustion products remain in the tube after combustion, due to the reduction of stagnant regions in each compartment by the directed flow of gas therethrough. A positive flow direction in each respective gas flow channel may be defined as a direction running from the inlet opening substantially directly to the outlet opening. In the combustion tube, substantially all of the combustion products flow through each successive channel with at least a component of flow direction substantially continuously in the positive flow direction. That is, the combustion products are generally caused to keep flowing onwards through channel after channel.

The secondary combustion chamber comprises a plurality of combustion compartments, arranged in a nested configuration and gas flow-linked in series. An advantage of the combustion tube is that combustion efficiency is improved. The extended path length through the combustion tube allows for a more complete combustion of the sample to take place. Not only is it possible for a greater proportion of the combustion products formed actually to be discharged from the tube for combustion analysis (resulting in increased sample component detection efficiency), but the combustion products may be discharged in a more concentrated manner (resulting in increased time efficiency).

Typically, a generally constant flow of a background carrier gas (such as argon or oxygen) is provided through the combustion tube and discharged from it as a discharge gas, to give a generally continuous background signal at the detector. With the directed flow arrangement, when a sample is combusted, a concentration in the discharge gas of the combustion products formed from that sample varies substantially as a top-hat function (or square-wave pulse shape). That is, as the combustion products reach the outlet opening of the outermost compartment of the secondary chamber, their concentration in the discharge gas rises rapidly from substantially zero to a given value. This concentration remains generally constant (subject, of course, to fluctuations generally occurring in the flow) while the combustion products are substantially completely discharged from the tube. Then, the concentration again falls rapidly back towards zero, since the dead spaces are so much smaller. Such a flow characteristic is much preferred to the standard, Gaussian distribution resulting from the prior art combustion tubes, since it allows the measurement accuracy to be improved. Such a flow characteristic is considered to be similar to that of a plug flow; i.e., for which the combustion products flow through the system substantially as a block or unit.

Preferably, the primary chamber feeds into the secondary chamber from an outlet opening shared with the inlet opening of the innermost compartment, more preferably at one end of the primary chamber.

Preferably, the inlet opening and the outlet opening of each compartment are substantially at opposite extremities of the respective compartment.

Preferably, the respective gas flow channel defined by each compartment is an elongate substantially annular channel from its inlet opening to its outlet opening.

Preferably, the plurality of combustion compartments define a substantially continuous gas flow conduit from the inlet opening of the innermost compartment to the outlet opening of the outermost compartment.

To help achieve the directed flow characteristic of the combustion tube, the gas flow channels are preferably relatively narrow. Preferably, each compartment has an inner and outer cylindrical sidewall and the gas flow channel is annular and defined therebetween. The difference in diameter between the sidewalls is preferably between approximately 0.5 and 20 mm, most preferably 2 mm.

Preferably, the plurality of combustion compartments comprise first to third combustion compartments arranged in series, the compartments thereby defining a gas flow conduit having first to third gas flow channels of increasing diameter and in alternating directions through the secondary chamber.

The combustion tube improves the combustion efficiency achievable for combusting a sample, by providing an extended gas flow conduit in which (further) combustion may take place. The secondary chamber is located over the outside of the primary chamber and comprises three, separate, but serially linked, compartments, arranged one outside the other. A sample initially combusted in the primary chamber is thereby provided with the opportunity to undergo further, substantially complete, combustion by passing along each of the three compartments in turn.

The relatively long gas flow conduit allows for combustion of the sample with a relatively high gas flow, which flow promotes mixing of the gases. A short length generally requires a slower gas flow, in order to give the gases sufficient time to be combusted. However, a slow flow does not promote gas mixing and also tends to result in more dead pockets forming in the combustion tube.

Since the secondary chamber is formed around the primary chamber, the overall length of the combustion tube may be reduced compared to the turbo tube. The relatively compact combustion tube requires less space, facilitating its integration into a combustion analyzer and reducing the footprint of the analyzer.

Preferably, the gas flow conduit is three or more times the length of the primary chamber, or at least that portion of the primary chamber surrounded by the secondary chamber. In some applications, it may be preferable to provide four or more combustion compartments in the secondary chamber.

Preferably, each respective combustion compartment comprises a longitudinal sidewall and one or more of the compartments comprises a respective static gas mixer fixed to the respective sidewall for effecting mixing of gases during their flow through the combustion tube.

As gases, in particular the sample, oxygen and/or combustion products, pass along the compartment, the static gas mixer disturbs the flow and redirects at least some of the gases, leading to mixing of the gases. This helps to improve the evenness of distribution of the gases, reducing the occurrence of local oxygen excesses and deficiencies and improving the efficiency of combustion in the combustion chamber.

Since the gas mixer is fixed to a sidewall and static, the resulting flow mixing characteristic of the combustion compartment is more reproducible and should not be affected by movement of the combustion tube. The static gas mixer is able to be effective at the high temperatures reached in combustion tubes.

The static gas mixer may take a number of forms. For example, the static gas mixer may comprise one or more vanes, ribs, projections, or other gas flow-interfering devices. Preferably, the static gas mixer comprises a plurality of longitudinally slanting ribs, or ridges. That is, the ribs are angled with respect to the longitudinal direction of the compartment, in which direction the gas flow generally travels. The first ribs have a first slant direction, which may be positively or negatively angled with respect to the longitudinal direction. The ribs disrupt the gas flow passing by or over them, causing at least a portion of the flow to be redirected in a swirling motion in the first direction, while some of the flow may continue in the longitudinal direction, resulting in beneficial local and general mixing.

Advantageously, the static gas mixer further comprises a plurality of longitudinally slanting second ribs, having a second, opposing slant direction. These cause at least a portion of the flow to be redirected in the second direction. This provides for increased flow disturbance, in different senses, leading to even better local and overall mixing of gases. Preferably, the first and second ribs are separated longitudinally along the compartment, so that one set of ribs can have its flow-disturbing effect before the other set. This can help to extend the distance over which the mixing is achieved.

Combining the plurality of combustion compartments with one or more static gas mixers provides an extended opportunity for combustion with increased gas mixing, to provide improved combustion efficiency to the combustion tube. At the same time, arranging the secondary chamber around the primary chamber helps to provide a relatively compact combustion tube, which in turn helps to reduce the footprint of a combustion analyzer to which it is to be fitted.

The ribs extend in a lateral direction from the sidewall(s) to which they are fixed. Preferably, the ribs extend around 75% of the lateral distance from their respective sidewall to the respective, next-outwardly-adjacent sidewall. The optimum gap size between the ribs and a respective outer sidewall is subject to a number of constraints and is best determined empirically. A gap of zero (i.e., rib height being 100% of the lateral distance) should provide the best flow performance for transferring gases through the combustion tube. A greater gap should improve the mixing performance of the combustion tube. A gap of around a quarter of the lateral distance between inner and outer sidewalls provides a beneficial compromise between considerations of flow performance, mixing performance and combustion tube manufacture.

The static gas mixer(s) described above may be provided in any of the above or below combustion tubes, to improve the combustion efficiency still further by promoting mixing of the sample and/or combustion products with oxygen during its/their passage through the tubes.

In order to promote (further) combustion in the combustion compartments, preferably a supply of oxygen is provided into the second innermost compartment. Preferably, the oxygen supply inlet is provided to the second innermost compartment at the same end as that into which the combustion products are introduced from the innermost compartment.

Advantageously, all inlets and outlets to the combustion tube itself are provided, and therefore all substances are supplied to and discharged from the combustion tube, at the same end of the combustion tube. This allows for an overall shorter combustion tube, thereby reducing the overall size of a combustion analyzer in which it is installed—an important consideration for bench space in a laboratory. This also results in easier servicing of the combustion tube or analyzer, since only one region of the instrument needs to be accessed to remove the tube for cleaning or replacement.

Preferably, the combustion tube is formed as one piece. This helps to ensure stable flow characteristics through the tube, since the various chambers and compartments remain in fixed spaced relation to one another.

According to another aspect of the invention, there is provided a method of combusting a sample in a combustion tube for combustion analysis of the sample, the combustion tube comprising: a primary combustion chamber; and a secondary combustion chamber disposed around the primary chamber and comprising a plurality of combustion compartments, each successive compartment being disposed around the preceding compartment and each compartment defining a respective gas flow channel having an inlet opening at one end and an outlet opening at the opposite end, each successive gas flow channel sharing its inlet opening with the outlet opening of the preceding channel, the method comprising the steps of: supplying to the primary chamber a sample and combusting the sample therein to form first combustion products; and passing the first combustion products into the secondary chamber and further combusting the first combustion products to form second combustion products, wherein a positive flow direction in each respective gas flow channel is defined as a direction running from its inlet opening substantially directly to its outlet opening and substantially all of the combustion products flow through each successive channel with at least a component of flow direction substantially continuously in the positive flow direction.

Preferably, the first and/or second combustion products enter each combustion compartment through its inlet opening and exit the compartment through its outlet opening, wherein the inlet opening and the outlet opening of each compartment are substantially at opposite extremities of the respective compartment.

Preferably, the plurality of combustion compartments define a substantially continuous gas flow conduit from the inlet opening of the innermost compartment to the outlet opening of the outermost compartment and the first and/or second combustion products follow a path through the secondary combustion chamber substantially defined by the gas flow conduit.

The features described above with reference to respective aspects of the invention are not limited to those aspects and may be applied to other aspects of the invention. Combinations of individual, or groups of, features from one combustion tube or method may be made with individual, or groups of, features from one or more other combustion tubes or methods, to provide mutually beneficial configurations. Such combinations or replacements of features also form part of the invention.

The term combustion products is used here to mean any substances present in the combustion tube during or following the combusting step and this may include the sample and other substances, such as oxygen or a carrier gas, and their respective constituents, both in pre-combustion and post-combustion forms, whether fully or incompletely combusted.

Other preferred features and advantages of the invention are set out in the description and in the dependent claims which are appended hereto.

BRIEF DESCRIPTION OF THE DRAWINGS

The invention may be put into practice in a number of ways and some embodiments will now be described, by way of non-limiting example only, with reference to the following figures, in which.

DETAILED DESCRIPTION

Figure 1:
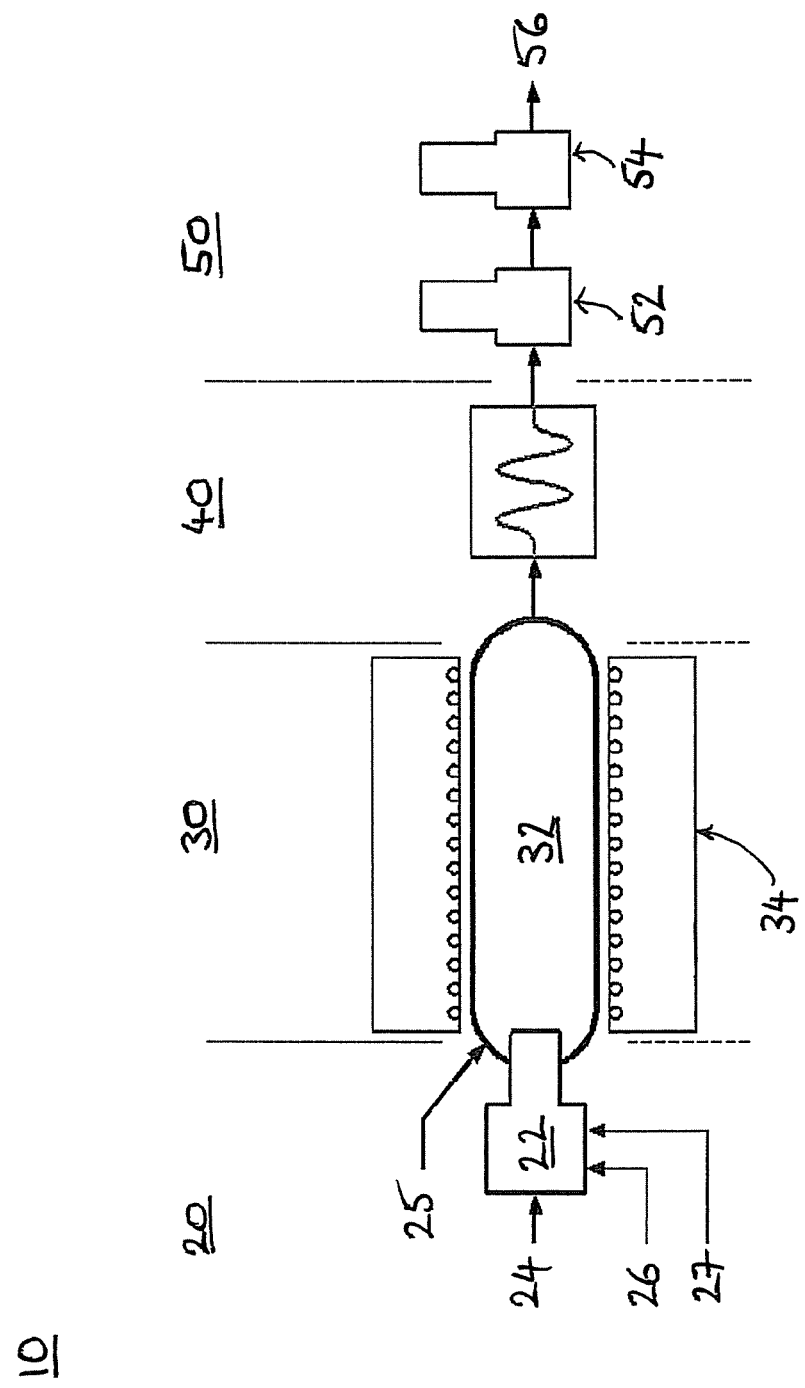
FIG. 1 shows a schematic layout of a typical, prior art combustion analyzer.
Figure 2:
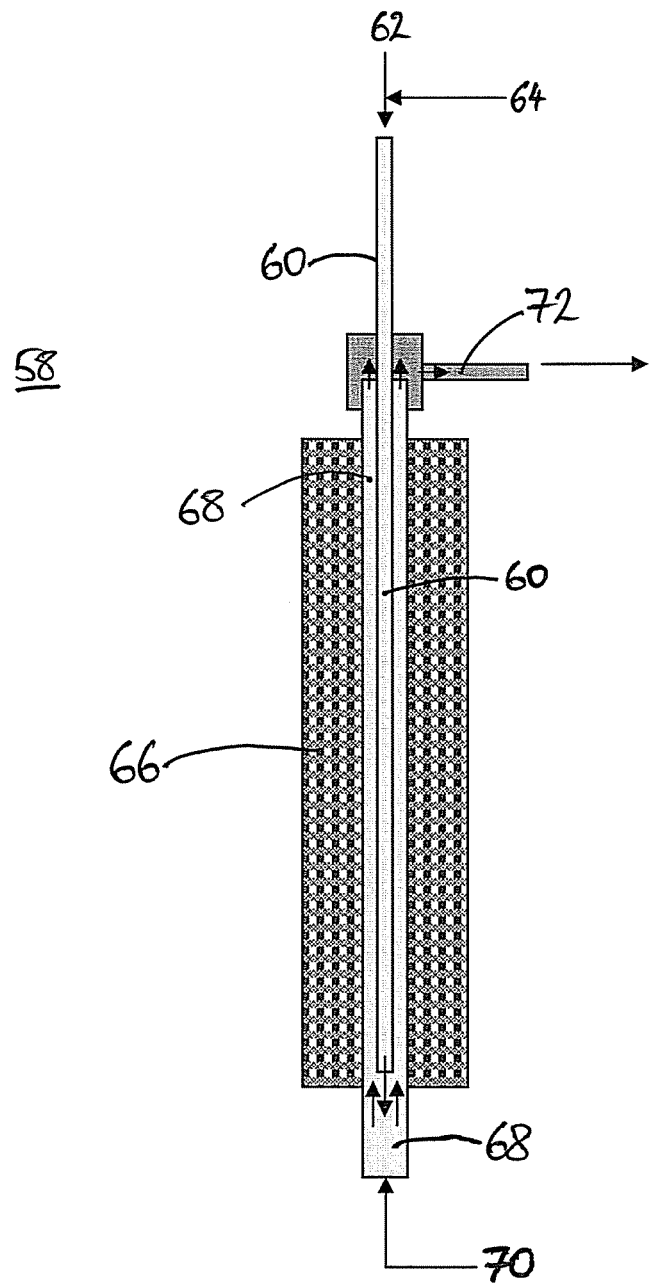
FIG. 2 shows a cross-sectional view of a prior art combustion tube.
Figure 3:
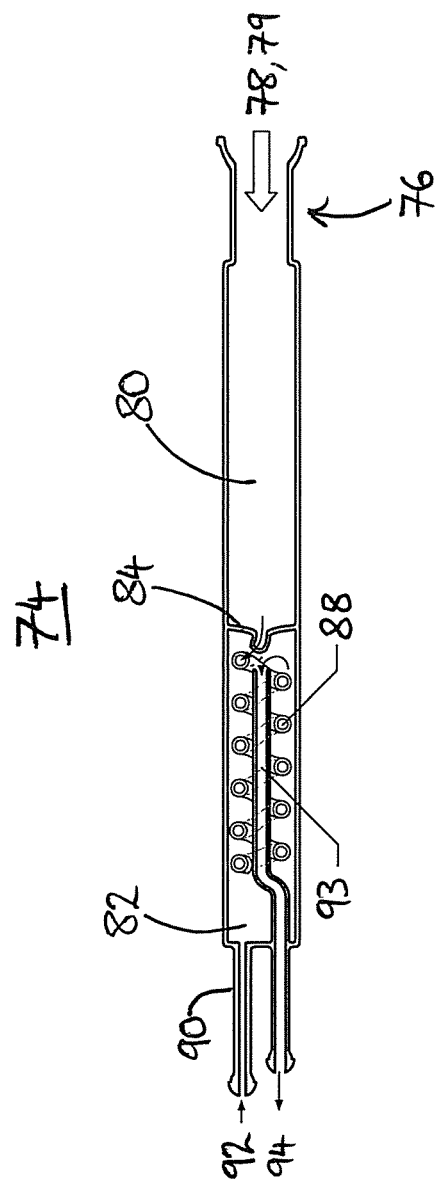
FIG. 3 shows a cross-sectional view of another prior art combustion tube.
Figure 4:
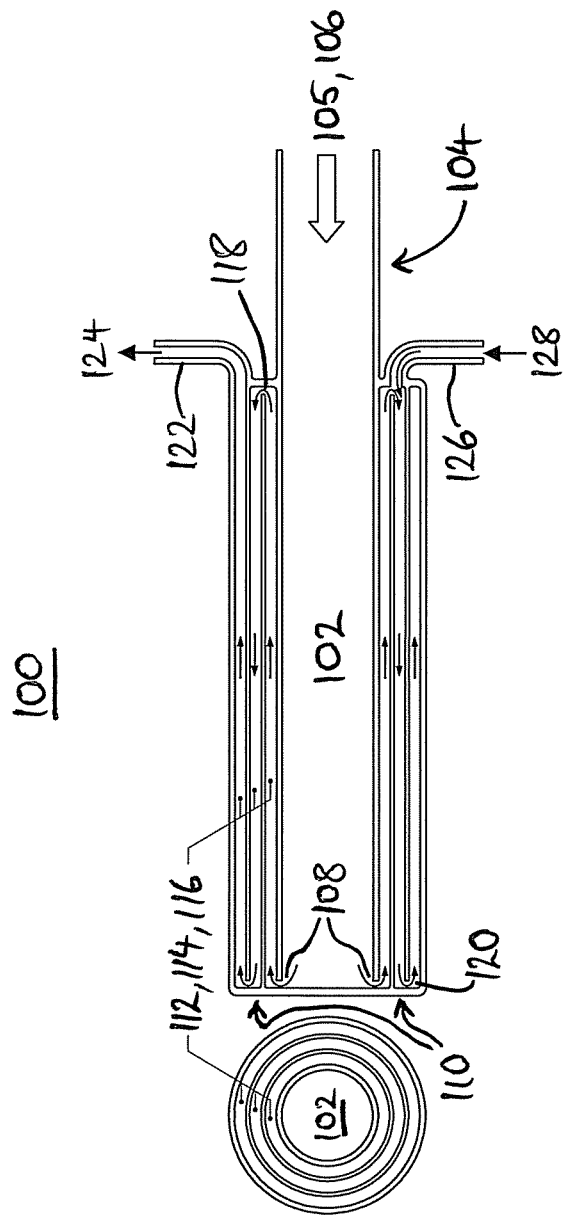
FIG. 4 shows lateral and longitudinal cross-sectional views of a combustion tube according to a first embodiment.

Referring to FIG. 4, there is shown a longitudinal cross section of a combustion tube 100. There is also shown, to the left, a lateral cross section of the tube, taken at an intermediate location along its length.

The combustion tube 100 comprises a primary combustion chamber 102 having at one end an inlet port 104, for receiving a supply of a sample 105, a supply of oxygen 106 and the like, and, at the opposite end, an opening 108, for discharging gases from the chamber. The opening 108 leads directly into a secondary combustion chamber 110, which surrounds a portion of the primary combustion chamber 102, and could be described as being folded back over the outside of the primary chamber. In this embodiment, the combustion tube has a generally cylindrical form, so that the secondary chamber 110 has the form of an annular tube.

The secondary chamber 110 comprises three, separate combustion compartments 112,114,116, arranged in a nested configuration, with the first compartment 112 being formed immediately adjacent and around the primary combustion chamber 102, the second compartment 114 being formed outside the first, and the third compartment 116 being formed outside the second. Each compartment 112,114,116 has a respective inner and outer, longitudinal sidewall, defining therebetween a respective gas flow channel, each successive channel in the form of an annular tube of increasing diameter.

Each compartment 112,114,116 has an inlet end having an inlet opening, for receiving a flow of gas, and an outlet end having an outlet opening, for discharging the flow of gas. The inlet end of the first compartment 112 is at the outlet end of the primary combustion chamber 102 and the inlet opening into the first compartment is provided by the opening 108. In this embodiment the various openings are full, circumferential openings, although other forms of opening may alternatively be used. The first gas flow channel runs from the inlet opening 108 to the outlet opening 118 of the first compartment 112, around the primary chamber 102 and towards the inlet end of the primary chamber. The inlet end of the second compartment 114 is at the outlet end of the first compartment 112 and the inlet opening into the second compartment is provided by the opening 118. The second gas flow channel runs from the inlet opening 118 to the outlet opening 120 of the second compartment 114, around the first compartment 112 and towards outlet end of the primary chamber 102. Finally, the inlet end of the third compartment 116 is at the outlet end of the second compartment 114 and the inlet opening into the third compartment is provided by the opening 120. The third gas flow channel runs from the inlet opening 120 to an outlet tube 122, around the second compartment 114 and towards the inlet end of the primary chamber 102. The outlet tube 122 is for discharging combustion products 124 from the combustion tube 100, for subsequent analysis thereof.

Connected to the secondary chamber 120 is an oxygen supply tube 126 for providing a further supply of oxygen 128 into the secondary chamber. The oxygen supply tube 126 opens into the second compartment 114 of the secondary chamber 120, at its inlet end, close to the opening 118 for receiving gases from the first compartment 112.

In use, a supply of a sample 105 and a supply of oxygen 106 are provided to the primary combustion chamber 102, via the inlet port 104. The combustion tube 100 is heated by a heater (not shown) which surrounds the tube. The sample 105 is at least partially combusted in the primary chamber 102. The resulting gases—first combustion products, which may include uncombusted sample, intermediate combustion products and oxygen, as well as completely combusted sample components—flow to the outlet end and pass through the opening 108 into the secondary combustion chamber 110. The first combustion products flow though each combustion compartment in series, travelling in alternating directions along each successive compartment, as shown by the arrows in FIG. 4. As the first combustion products flow along the compartments 112,114,116, further combustion takes place. To help improve the combustion of the first combustion products, a further supply of oxygen 128 is provided via tube 126 into the inlet end of the second compartment 114. Here, the oxygen 128 mixes with the combustion products entering the second compartment 114 from the first compartment 112 and helps to reduce the occurrence of local oxygen deficiencies. The mixture flows through the second compartment 114 and back through the third compartment 116, allowing for further, substantially complete, combustion of the sample to form second combustion products. The second combustion products exit the combustion tube 100 through the outlet tube 122, for further analysis.

In the combustion tube 100, the compartments 112,114, 116 of the secondary chamber 110 lead from one directly into the next, in sequence, via a respective, shared opening 118, 120. The openings 108,118,120 into each compartment are located at an end or extremity of each compartment, so that gas flowing into the inlet openings has no option but to flow towards the respective outlet openings, as a directed flow. If a positive flow direction is defined in each compartment as the direction running substantially directly from the inlet opening to outlet opening of that compartment, then it can be said that the combustion products flow in the positive flow direction through the secondary chamber 110. In particular, with the combustion tube 100, substantially all of the combustion products flow through the secondary chamber 110 with at least a component of flow direction substantially always in the positive flow direction (i.e., the gases do not generally flow in the opposite, negative flow direction, nor generally do they settle in stagnant regions). The combustion products are carried through the secondary chamber 110 generally as a continuous flow, which is considered to approach a plug flow. This means that sample throughput times can be reduced, as the sample gases pass through the secondary chamber substantially as a whole, instead of languishing in dead spaces (which extends the duration of their passage through the chamber).

Correspondingly, the flush time between samples can be reduced, since a flushing gas can quickly pass through the secondary chamber 110 and urge any residual sample gases out of the chamber. Because the stagnant regions are reduced, the amount of residual sample gases is also reduced. This not only further helps to speed up flush-out times, but also means a greater proportion of the combustion products from the sample can be discharged from the combustion tube 100 for detection. The relatively concentrated discharge from the combustion tube 100 of combustion products from a particular sample permits faster and more accurate analysis.

Typically, a background gas, usually argon or oxygen, flows through a combustion analyzer and gives a generally constant background signal. When the combustion tube 100 discharges combustion products from a sample, the signal rises sharply to a level which remains generally steady as discharge continues. When the combustion products have been discharged from the tube, the signal level falls rapidly back to the background signal level. This type of flow has the general form of a top-hat function, or square-wave pulse, and approaches a plug flow.

In the remaining figures, like or same features are referred to with the same reference numerals.

Figure 5:
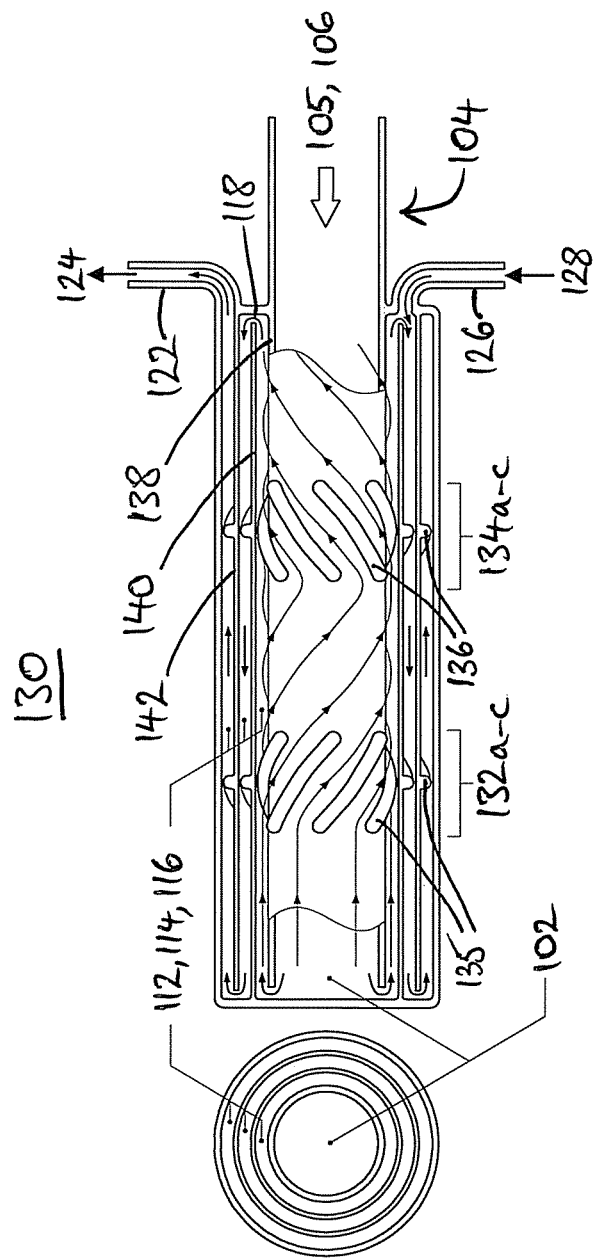
FIG. 5 shows lateral and longitudinal cross-sectional views of a combustion tube according to a second embodiment.

FIG. 5 shows, in schematic cross sections, a combustion tube 130 according to another embodiment of the invention. The combustion tube 130 is similar to the combustion tube 100 shown in FIG. 4, but further comprises a number of static gas mixers 132a-c,134a-c in the secondary chamber 110. In this embodiment, there are two static gas mixers in each compartment 112,114,116, formed on the inner of the two longitudinal sidewalls for each compartment and separated longitudinally from each other. In this embodiment, a static gas mixer comprises a number of longitudinally slanting ribs 135,136, formed circumferentially around the respective sidewall.

So, the inner sidewall 138 of the first compartment 112 has fixed thereto, at a location intermediate the inlet end and a midpoint, a first static gas mixer 132a. The static gas mixer comprises six longitudinally slanting ribs 135, which lie at an angle of around 45° to the longitudinal direction and are evenly spaced around the circumference of the sidewall 138. The ribs 135 are formed on the sidewall with a positive rotation/screw direction.

At a location intermediate the midpoint and the outlet end of the first compartment 112, the inner sidewall 138 has fixed thereto a second static gas mixer 134a. The static gas mixer comprises six longitudinally slanting ribs 136, which lie at an angle of around 45° to the longitudinal direction and are evenly spaced around the circumference of the sidewall 138. The ribs 136 are formed on the sidewall with a negative rotation/screw direction. FIG. 5 shows a cut-away view of a portion of the sidewall 138 with the static gas mixers 132a, 134a fixed thereto.

Similarly, the inner sidewall 140 of the second compartment 114 has first and second static gas mixers 132b, 134b fixed thereto, at similar locations. However, since the inlet and outlet ends are reversed for the second compartment, the order of the static gas mixers is also reversed in this embodiment. Finally, the inner sidewall 142 of the third compartment 116 has first and second static gas mixers 132c, 134c fixed thereto, at locations corresponding to those for the first compartment again.

The ribs 135,136 are welded or fused to the sidewalls and are thereby fixed and otherwise static, so that their mixing characteristics are not affected by movement of the combustion tube. The ribs are preferably made of the same material as the combustion tube itself—which is preferably quartz—so that they are substantially unaffected by the high operating temperatures of the combustion tube. The dimensions of the ribs are chosen so that a relatively small gap remains between the top—the laterally (radially) outermost part—of each rib and the respective outer sidewall of the compartment comprising the rib. The gap is preferred to be around 25% of the lateral distance between the inner and outer sidewalls of a compartment; that is, the ribs have a lateral height, preferably around 75% of the lateral distance. This is considered to provide a suitable balance between the demands for good flow performance, good mixing performance and ease of manufacture.

In use, a sample 105 and oxygen 106 are supplied to the primary combustion chamber 102, in which at least partial combustion takes place. As with combustion tube 100, the first combustion products then pass into the secondary combustion chamber 110 and flow successively through the first to third combustion compartments 112,114,116, in which further combustion takes place. Oxygen 128 is added to the second compartment 114, to facilitate and improve such further combustion.

As the first combustion products pass through the first compartment 112 of the combustion tube 130, the first static gas mixer 132a disturbs the flow and redirects at least some of the gases, which leads to mixing of the gases. In particular, the slanting ribs 135 impart a swirling motion to at least some of the gases, while some of the gases flow straight over the ribs, through the gaps above them. Some exemplary gas flow routes are shown by arrowed lines in FIG. 5. The differences in gas flow speeds of the gases swirling close to the inner sidewall 138, the gases swirling around the outer parts of the compartment 112 and the gases flowing through the gaps lead to localised turbulence which results in thorough mixing of the gases at and downstream of the static gas mixer 132a.

A similar effect is achieved by the second static gas mixer 134a downstream of the first static gas mixer 132a, but with an opposite swirling direction. In combination, the static gas mixers 132a,134a are able to provide very good local, as well as overall, mixing of the gases, to help improve the efficiency of combustion of the first combustion products. Repeated over all three of the combustion compartments 112,114,116, the static gas mixers 132a-c,134a-c achieve beneficial gas mixing. The relatively long gas flow path through the secondary chamber 110 also provides an extended opportunity for combustion to take place, so that the achievable completeness of sample combustion is high.

With this embodiment, the flushing out of the combustion tube is enhanced. As a result of the operation of the static mixers, the gases flowing through the first to third combustion compartments are well mixed and substantially homogeneous. This helps to prevent the separation out of heavier gaseous components, which could collect at the bottom of the combustion tube and lead to slow flushing out times, in particular from the third combustion compartment. In addition, the static gas mixers cause the gases to rotate or swirl somewhat, helping to discharge the gases from the third compartment, into the outlet tube 122.

Figure 6:
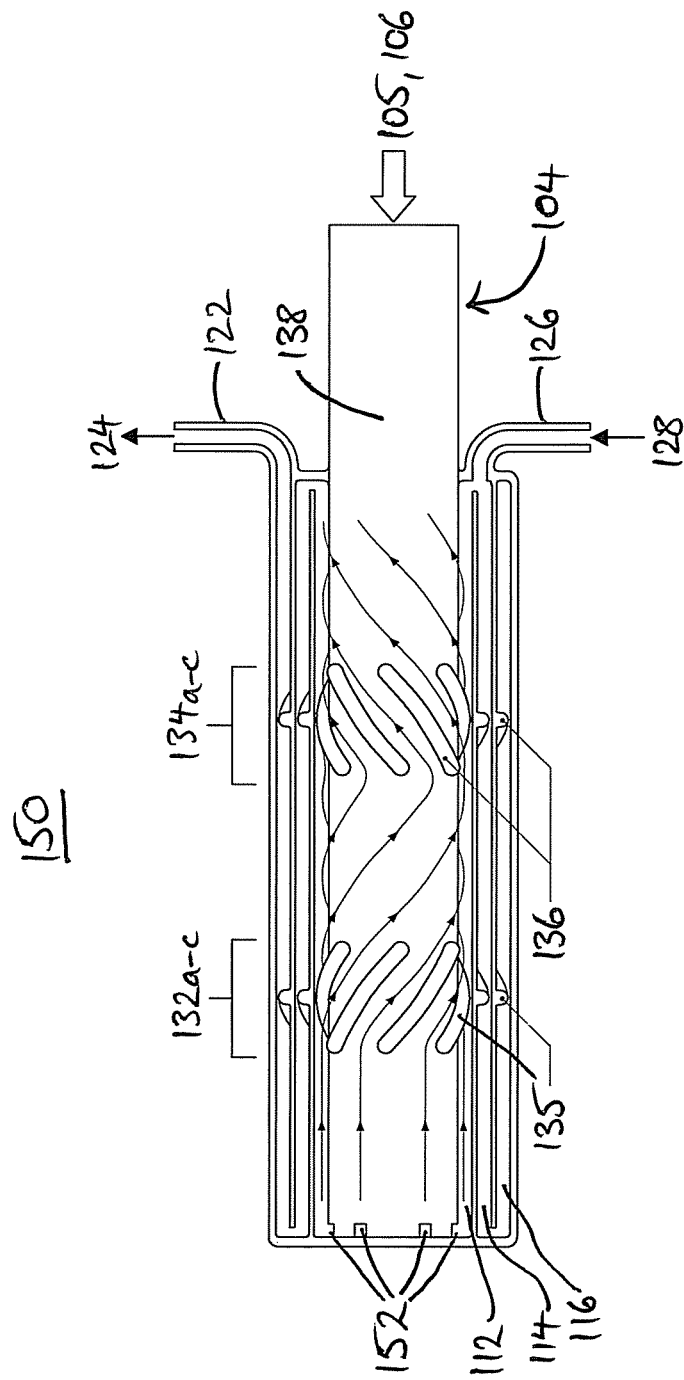
FIG. 6 shows a cross-sectional view of a combustion tube according to a third embodiment.

FIG. 6 shows a partial cut-away sectional view of a combustion tube 150 according to a further embodiment of the invention. The partial cut-away view shows the entire length of the inner sidewall 138 of the first combustion compartment 112. The combustion tube 150 is very similar to the combustion tube 130. However, the full, circumferential opening 108 between the primary combustion chamber 102 and the first combustion compartment 112 has been replaced by a number of smaller apertures 152, spaced apart from each other around the circumference of the sidewall 138 at the outlet end of the primary chamber. The apertures 152 correspond in number to and are in register with the circumferential spaces between adjacent ribs 135 of the first static gas mixer 132a. They need not be so, however, and the effect of this arrangement will, in any case, depend on the gas flow speeds through the combustion tube 150. Otherwise, the configuration and function of the combustion tube 150 is as for the combustion tube 130.

In the combustion tubes of the above embodiments, the combustion products may be relatively quickly passed through and discharged from the combustion tube, resulting in a shorter overall analysis time. The secondary chamber is a relatively long, narrow gas flow conduit, folded back on itself a number of times. The chamber has hardly any dead spaces in which gases can stagnate, and the swirling motion of the gases due to the static gas mixers helps to ensure that even small "corners" of the combustion tube are well flushed. Experiments have shown that the flow characteristics of the above combustion tubes approach that of a plug flow. Changes in the composition of gases supplied to the combustion tube are tracked shortly afterwards by corresponding changes in the composition of gases discharged from the combustion tube, with only a relatively small amount of broadening. In addition to lowering the analysis time, this also contributes to the sensitivity and accuracy of a combustion analyzer in which the combustion tube is used, because the detected signal will be more intense and better defined.

Indeed, the time taken to flush out a combustion tube according to one of the above embodiments may be significantly shorter than the time taken with the turbo tube. The flush-out time for the turbo tube is approximately 120 seconds, whereas the above combustion tubes are capable of providing a flush-out time of less than 30 seconds.

The length of the gas flow conduit in the secondary chamber provides a relatively extended opportunity for combustion to take place, helping to ensure that the combustion is substantially complete. A greater proportion of the sample may thereby be detected as the relevant oxides of the constituents of the sample.

The provision of static gas mixers further contributes to the improvement in the combustion efficiency, by providing very good local and overall mixing of the gases during their passage through the combustions tube.

Because of its layout, the combustion tube is able to occupy considerably less space in a combustion analyzer, being significantly shorter than, for example, the turbo tube. The combustion tube is also easier to integrate into a combustion analyzer. This is, in particular, because, in the above embodiments, all inlet and outlet ports/openings/tubes are situated at one end of the combustion tube. This provides the advantages that the space needed for the various connections can be shared; the tubing connected to the various inlet/outlet ports/openings/tubes can be kept relatively short; and only one side of the combustion tube needs to be accessed for maintenance and repair.

In the embodiments above, an odd number of combustion compartments are employed, so that all inlet and outlet connections can be made at the same end of the combustion tube. However, connections on both ends of a combustion tube may alternatively be provided; for example, in the case of a secondary combustion chamber having four combustion compartments. The number and dimensions of the combustion compartments are determined by a number of practical considerations, which include a) the total volume of all of the combustion compartments should preferably be large enough to achieve a sufficiently long retention time for the combustion gases, at a given flow rate; b) the cross-sectional area of individual combustion compartments should preferably be small enough to obtain good "plug flow" properties; c) the cross-sectional area of the individual compartments should preferably be large enough to avoid too high a flow resistance, and also to accommodate static gas mixers, where provided; and d) such a combustion tube must be producible at a reasonable cost. Taking these considerations into account, it is felt that a combustion tube with three combustion compartments around a primary combustion chamber is close to optimum. However, a higher or lower number of combustion compartments may alternatively be provided.

The dimensions chosen for the combustion tube depend on a number of variables, such as the desired retention time for the gases, the gas flow rates, the types of sample, the sample introduction method, among others. A general indication of suitable dimensions for a combustion tube is given below. The preferred values given are those for a prototype combustion tube. However, such values for and ranges in the dimensions are not to be considered as limiting.

The combustion compartments may have a length from 100 to 400 mm, with a preferred length of 160 mm. The lateral (radial) distance between the inner and outer sidewalls of each combustion compartment may vary from 0.5 to 20 mm, with a preferred distance of 2 mm. The inner diameter of the primary combustion chamber may vary from 10 to 50 mm, with a preferred diameter of 25 mm. This diameter is considered to be suitable for existing and future sample introduction apparatuses, and, in particular, is large enough to enable solid samples to be introduced on a crucible. The length of the neck of the primary combustion chamber (i.e., the length of the inlet port 104) may vary from 20 to 150 mm, with a preferred length of 50 mm.

The preferred combustion tube is accordingly approximately half the length of the conventional turbo tube, while its width is only slightly greater. As a result, the length of the combustion tube heater and insulation may be correspondingly reduced. Furthermore, it has been found that manufacturing the combustion tube is easier than manufacturing the turbo tube.

In the above embodiments, each static gas mixer includes six longitudinally slanting ribs. Theoretically, any number of such ribs could be used per static gas mixer, but practically—depending on the diameter of the sidewalls—a number from 4 to 12 should be sufficient.

For optimum mixing of gases in the combustion compartments, it is preferred for there to be two static gas mixers in each compartment, the two mixers having oppositely slanting ribs. However, some of the compartments may include only one static gas mixer, or even none, or indeed more than two static gas mixers, depending on the structure and application of the combustion tube. Also, while it is preferred to provide pairs of oppositely slanting ribs in each combustion compartment, the order of the ribs may be reversed from the embodiments described above or ribs slanting only in one direction may alternatively be provided.

The static gas mixer may be provided by vanes or other gas flow-disturbing protrusions, but is preferably provided by a number of longitudinally slanting ribs. Many different configurations of the ribs may be provided and the selection and dimensioning of the ribs is best determined by experiment. One currently preferred rib design performs satisfactorily, although improvements to it may be possible. Each rib is placed at an angle of approximately 45° to the longitudinal direction of the combustion tube. The length of each rib is about 30 mm. The optimum gap between the top of a rib and the outer sidewall (in a lateral or radial direction) is also best determined experimentally. A gap of zero (i.e., a full-height rib) should give the best "plug flow" performance, while a larger gap should provide better mixing. A compromise between these considerations and manufacturing criteria has resulted in a preferred gap of approximately 0.5 mm, which is around 25% of the preferred distance between the inner and outer sidewalls (i.e., the rib is around 75% of the lateral distance between the sidewalls). Where two static gas mixers are provided in the same combustion compartment, it is preferred to position them with a longitudinal spacing of around 40 mm, provided at the middle point of the compartment.

The provision of additional oxygen into the secondary chamber is advantageous, since it permits less oxygen to be provided in the primary combustion chamber, so that combustion hotspots (that is, local peaks in temperature, resulting from vigorous combustion) can be avoided. The oxygen supply tube may be connected to the secondary combustion chamber at any location, but clearly it is preferable to supply the oxygen relatively early on in the passage of gases through the secondary chamber. While the layouts in FIGS. 4 to 6 show the outlet tube 122 and the oxygen supply tube 126 at the top and bottom, respectively, of the combustion tubes, this need not be the case. The tubes may be the other way round, or horizontally side-by-side, or in any other suitable arrangement.

The combustion compartments described above are each generally uniform in cross section and this is preferred, for the sake of improving the flow characteristics of the combustion tube. The combustion compartments may have different, or varying, profiles, but preferably gases flow into each compartment at one end and out at the other end and there are substantially no dead spaces in which the gases could stagnate.

The benefits of the secondary combustion chamber, being divided into a number of serially linked combustion compartments may be enjoyed in a combustion chamber not having a central, primary combustion chamber, around which the secondary chamber is formed. For example, in a similar manner to the turbo tube, the primary combustion chamber and the secondary combustion chamber may be separated axially, or longitudinally, from each other and linked by an opening in a partition separating the two chambers. The partition opening may be central, so that gases flow through the compartments from the innermost to the outermost, or it may be circumferential, so that gases flow through the compartments from the outermost to the innermost. The secondary chamber may otherwise be configured in a similar manner to those described above; namely, features providing improved gas mixing and features providing improved flow characteristics may be provided with the chamber.

The beneficial gas flow mixing provided by the static gas mixer described above may be provided in any combustion compartment having a sidewall to which the static gas mixer may be fixed. Such a compartment may be a simple, single-chamber combustion tube comprising the static gas mixer internally on its sidewall. Alternatively, the combustion tube may comprise a plurality of combustion compartments, arranged in series and comprising one or more static gas mixers. Alternatively still, the combustion tube may comprise a primary combustion chamber separated axially from a secondary combustion chamber, which is divided into a number of combustion compartments, one or more of the chambers or compartments comprising a static gas mixer or mixers. Where a plurality of combustion compartments is provided, the static gas mixer(s) could be disposed on either or both of the inner and the outer sidewall of the or each compartment.

Other combinations, modifications, or alterations to the features of the above combustion tubes will be readily apparent to the skilled person and are intended to form part of the invention.

The invention may be employed for various applications in, for example, the chemical, refinery, hydrocarbon, petrochemical, and food and beverage sectors. The invention may be used in the analysis of solid, high-viscosity, liquid or gaseous samples. In particular, the invention may be used in the analysis of refinery products, such as gasoline and diesels.

What is claimed is:

1. A combustion tube for receiving a sample for combustion thereof to form combustion products, the combustion tube comprising:
   a primary combustion chamber for receiving a sample for combustion thereof to form first combustion products; and a secondary combustion chamber for receiving the first combustion products for further combustion thereof to form second combustion products, the secondary chamber being disposed around the primary chamber and comprising a plurality of combustion compartments, each successive combustion compartment being disposed around the preceding combustion compartment and each combustion compartment defining a respective elongate and substantially annular gas flow channel having an inlet opening at one end and an outlet opening at the opposite end, wherein each successive as flow channel shares its inlet opening with the outlet opening of the preceding channel;

wherein each respective combustion compartment comprises a longitudinal sidewall and each combustion compartment comprises a respective first static gas mixer fixed to the respective sidewall for effecting mixing of gases during their flow through the combustion tube, each first static gas mixer comprising a respective plurality of ribs fixed on the respective sidewall within the respective combustion compartment and formed in accordance with either a positive or a negative screw direction, wherein one or more of the combustion compartments further comprises a second static gas mixer fixed to the respective combustion compartment sidewall, the second static gas mixer comprising another plurality of ribs fixed on the sidewall of the respective combustion compartment and formed in accordance with a screw direction that is opposite to the screw direction associated with the first static gas mixer within the same respective combustion compartment.

2. The combustion tube of claim 1, wherein each second static gas mixer is disposed between the outlet opening and a midpoint of the respective combustion compartment and each first static gas mixer is disposed between the inlet opening and the midpoint of the respective combustion compartment.

3. A combustion tube for receiving a sample for combustion thereof to form combustion products, the combustion tube comprising:

a primary combustion chamber for receiving a sample for combustion thereof to form first combustion products; and a secondary combustion chamber for receiving the first combustion products for further combustion thereof to form second combustion products, the secondary chamber being disposed around the primary chamber and comprising a plurality of combustion compartments, each successive combustion compartment being disposed around the preceding combustion compartment and each combustion compartment defining a respective elongate and substantially annular gas flow channel having an inlet opening at one end and an outlet opening at the opposite end, wherein each successive gas flow channel shares its inlet opening with the outlet opening of the preceding channel;

wherein each respective combustion compartment comprises a longitudinal sidewall and each combustion compartment comprises a respective first static gas mixer fixed to the respective sidewall for effecting mixing of gases during their flow through the combustion tube, each first static gas mixer comprising a respective plurality of ribs fixed on the respective sidewall within the respective combustion compartment and formed in accordance with either a positive or a negative screw direction, wherein each sidewall having a static gas mixer fixed thereto is separated from a laterally adjacent sidewall by a respective first lateral distance and the static gas mixer has a lateral height approximately three-quarters of the respective first lateral distance.

4. The combustion tube of claim 1, wherein a second one of the combustion compartments has an inlet end for receiving first combustion products from an innermost one of the combustion compartments, the combustion tube further comprising an oxygen supply inlet connected to the second combustion compartment at its inlet end for receiving oxygen for the further combustion of the first combustion products.

5. The combustion tube of claim 4, wherein the number of combustion compartments is odd, the primary chamber comprises an inlet port for receiving a sample, and an outermost one of the combustion compartments comprises a discharge outlet for discharging second combustion products from the combustion tube, and each of the inlet port, the discharge outlet, and the oxygen supply inlet, are arranged at the same end of the combustion tube.

6. The combustion tube of claim 1, the combustion tube being formed as one piece.

7. The combustion tube of claim 1, wherein the ribs of either each first static gas mixer or of each second static gas mixer are equally spaced circumferentially around the respective sidewall.

8. The combustion tube of claim 1, wherein the primary chamber comprises an outlet opening, and an innermost gas flow channel shares its inlet opening with the outlet opening of the primary chamber.

9. The combustion tube of claim 1, wherein the inlet opening and the outlet opening of each combustion compartment are substantially at opposite extremities of the respective combustion compartment.

10. The combustion tube of claim 1, wherein the plurality of combustion compartments define a substantially continuous gas flow conduit from the inlet opening of an innermost one of the combustion compartments to the outlet opening of an outermost one of the combustion compartments.

11. The combustion tube of claim 1, wherein each respective combustion compartment comprises an inner cylindrical sidewall and an outer cylindrical sidewall defining therebetween the respective annular gas flow channel having inner and outer diameters, the difference between the inner and outer diameters being between approximately 0.5 and 20 mm, preferably 2 mm.

12. The combustion tube of claim 3, wherein the primary chamber comprises an outlet opening, and an innermost gas flow channel shares its inlet opening with the outlet opening of the primary chamber.

13. The combustion tube of claim 3, wherein the inlet opening and the outlet opening of each combustion compartment are substantially at opposite extremities of the respective combustion compartment.

14. The combustion tube of claim 3, wherein the plurality of combustion compartments define a substantially continuous gas flow conduit from the inlet opening of an innermost one of the combustion compartments to the outlet opening of an outermost one of the combustion compartments.

15. The combustion tube of claim 3, wherein a second one of the combustion compartments has an inlet end for receiving first combustion products from an innermost one of the combustion compartments, the combustion tube further comprising an oxygen supply inlet connected to the second combustion compartment at its inlet end for receiving oxygen for the further combustion of the first combustion products.

16. The combustion tube of claim 15, wherein the number of combustion compartments is odd, the primary chamber comprises an inlet port for receiving a sample, and an outermost one of the combustion compartments comprises a discharge outlet for discharging second combustion products from the combustion tube, and each of the inlet port, the discharge outlet, and the oxygen supply inlet, are arranged at the same end of the combustion tube.

17. The combustion tube of claim 3, the combustion tube being formed as one piece.

* * * * *

UNITED STATES PATENT AND TRADEMARK OFFICE
CERTIFICATE OF CORRECTION

PATENT NO. : 8,758,698 B2  
APPLICATION NO. : 12/054006  
DATED : June 24, 2014  
INVENTOR(S) : Smeets et al.

Page 1 of 1

It is certified that error appears in the above-identified patent and that said Letters Patent is hereby corrected as shown below:

Title Page:

Item (73) Assignee:

Please replace "Thermo Fisher Scientific Inc., Waltham, MA (US)"  
with -- Thermo Electron Manufacturing Ltd., Cambridge, UK --

Signed and Sealed this  
Twenty-third Day of February, 2016

Michelle K. Lee  
*Director of the United States Patent and Trademark Office*